United States Patent
Kantner et al.

[11] Patent Number: 5,985,990
[45] Date of Patent: Nov. 16, 1999

[54] USE OF PENDANT FREE-RADICALLY POLYMERIZABLE MOIETIES WITH POLAR POLYMERS TO PREPARE HYDROPHILIC PRESSURE SENSITIVE ADHESIVE COMPOSITIONS

[75] Inventors: Steven S. Kantner, St. Paul, Minn.; Wilhelm Kuester, Kaarst, Germany

[73] Assignee: 3M Innovative Properties Company, St. Paul, Minn.

[21] Appl. No.: 09/091,782

[22] PCT Filed: Dec. 29, 1995

[86] PCT No.: PCT/US95/17079

§ 371 Date: Jun. 23, 1998

§ 102(e) Date: Jun. 23, 1998

[51] Int. Cl.⁶ ............ C08J 93/00; A61F 13/02; A61N 1/30

[52] U.S. Cl. .......... 524/765; 524/766; 524/767; 522/149; 522/153; 604/20; 604/180; 600/391; 424/448

[58] Field of Search ............ 604/20, 180; 600/391; 607/149, 152; 424/448; 522/149, 153; 524/765–767

[56] References Cited

U.S. PATENT DOCUMENTS

| | | | |
|---|---|---|---|
| 5,622,168 | 4/1997 | Keusch et al. | 128/640 |
| 5,674,275 | 10/1997 | Tang et al. | 607/152 |
| 5,859,112 | 1/1999 | Overbeck et al. | 524/460 |
| 5,868,136 | 2/1999 | Fox et al. | 128/640 |

FOREIGN PATENT DOCUMENTS

| | | | |
|---|---|---|---|
| 1153833 | 5/1969 | United Kingdom | C08F 27/12 |
| WO 94/12584 | 6/1994 | WIPO | C09J 123/08 |
| WO 95/00560 | 1/1995 | WIPO | C08F 8/00 |

*Primary Examiner*—Corrine McDermott
*Assistant Examiner*—Michael J. Hayes
*Attorney, Agent, or Firm*—Eloise J. Maki

[57] ABSTRACT

Cross-linked, hydrophilic pressure sensitive adhesive compositions, (meth)acrylate-functional polar polymers which serve as precursors to them, and medical products using such adhesives are disclosed. The cross-linked polymer is prepared by free-radically cross-linking reactive polymers that are functionalized with pendant polymerizable moieties. Medical products that include such compositions are biomedical electrodes, pharmaceutical delivery devices, and medical skin coverings such as wound dressings.

22 Claims, 2 Drawing Sheets

USE OF PENDANT FREE-RADICALLY POLYMERIZABLE MOIETIES WITH POLAR POLYMERS TO PREPARE HYDROPHILIC PRESSURE SENSITIVE ADHESIVE COMPOSITIONS

FIELD OF THE INVENTION

This invention relates to hydrophilic pressure sensitive adhesives, (meth)acrylate-functional polar polymers which serve as precursors to them, and medical products using such adhesives.

BACKGROUND OF THE INVENTION

Hydrophilic pressure sensitive adhesives are used in the medical field for a variety of skin-contacting applications as detailed in "An Overview of Skin Contact Applications for Pressure-sensitive Adhesives", D. G. Pierson, Tappi Journal, 73 (6), 101–107 (June, 1990). These applications include use as adhesives which absorb exudate from wounds, as ionically conductive adhesives in biomedical electrodes, and in iontophoretic (electrically enhanced) transdermal delivery of polar drugs.

Hydrophilic pressure sensitive adhesives are networks of a polar polymer, generally crosslinked and plasticized with a compatible humectant material such as glycerin or poly (ethylene glycol). Water, a salt, or a drug may also be included depending on the application. A relatively thick layer of adhesive is typically used (0.25 to 2.5 mm (10 to 100 mil) or greater).

Several approaches have been developed to prepare these hydrophilic pressure sensitive adhesives. They can be generated by delivering a moderate viscosity solution from solvent or water and drying (exemplified by U.S. Pat. No. 5,276,079); by extrusion coating a high viscosity precursor (exemplified by U.S. Pat. Nos. 4,674,512 and 4,593,053); by polymerization on-web of a low viscosity mixture of monomer, crosslinker, and humectant (exemplified by U.S. Pat. Nos. 4,524,087; 4,539,996; 4,554,924; and 4,848,353); and by crosslinking on-web a moderate viscosity precursor of polymer and humectant. For this final approach the crosslinking can be brought about by exposure of a non-functional polymer to high energy irradiation (exemplified by U.S. Pat. Nos. 4,699,146 and 4,750,482; and PCT Publication WO 93/10163), by mixing in a reactive crosslinking agent during the coating process (exemplified by U.S. Pat. Nos. 4,515,162 and 5,160,328; and PCT Publication WO 93/22380or by exposure of a vinyl functional polymer to a free radical source. Such vinyl functional polymers can be prepared by reaction of amine terminated poly(ethylene oxide) with, for example, vinyl dimethyl azlactone (e.g., PCT Publication WO 94/12585), reaction of isocyanate functional polyoxyalkylene oligomer with hydroxyethyl methacrylate (e.g., EPO Publication EP 271,292), and reaction of poly(vinyl ether/maleic anhydride) with allyl amine or allyl alcohol (e.g., British Publication GB 2,268,495). These approaches are applicable to a relatively narrow range of polar polymers and may require the use of an aprotic solvent during synthesis which must be removed.

SUMMARY OF THE INVENTION

A need exists for a method of functionalization of polar polymers which can be applied to a wider range of materials and that does not require specialized equipment or the use of aprotic solvent, yielding materials that can be rapidly and reliably crosslinked without generating concerns about potentially toxic or irritating unreacted low molecular weight monomers.

A need also exists for materials which allow for efficient manufacture of medical articles and devices in an integrated fashion, reducing the number of steps required and hence reducing waste and expense.

This invention concerns polar polymers which are functionalized with pendant free-radically polymerizable moieties to provide hydrophilic pressure sensitive adhesives when plasticized with humectants and exposed to a free radical source. When this free radical source is a photoinitiator, very rapid, reproducible, and complete crosslinking can be obtained with high intensity UV lights allowing for efficient manufacture of adhesive coated articles and tapes, especially when thick coatings of adhesive are desired. These materials are particularly suited for use as skin contacting pressure sensitive adhesives for medical use where high moisture vapor transmission rates or ionic conductivity may be important.

Thus, this invention provides a family of hydrophilic pressure sensitive adhesives based on plasticized polar networks. These networks are prepared by free-radically crosslinking reactive polymers which are functionalized with pendant polymerizable moieties.

This invention has several advantages. The precursor is low viscosity, readily processable, and solventless. The crosslink density is predetermined. The adhesives can rapidly and reliably be prepared without requiring specialized equipment and without generating concerns about potentially toxic or irritating unreacted low molecular weight monomers.

In one aspect of the invention, the method of functionalization involves reaction of an epoxy-functional acrylate or methacrylate with a carboxy-functional polymer to give acrylate or methacrylate moieties pendant from the backbone. An example of this method of functionalization is shown in Equation I below:

This type of functionalization has been applied to non-hydrophilic polymers in the past. Japanese Kokai JP 06138659 (Tamura Kaken) discloses the reaction of methacrylate copolymers with 3,4-epoxycyclohexyl methacrylate and formulates them with a diluent to give photosensitive etching resists. Japanese Kokai JP 63301282 (Nichiban) discloses the reaction of acrylic copolymers with glycidyl methacrylate to give pressure sensitive adhesives useful for protective sheets because they can by photocrosslinked (detackified) with UV to allow for easy removal. U.S. Pat. No 4,665,106 (Hitachi Chemical) discloses the copolymerization of glycidyl methacrylate with acrylic esters to give epoxy functional oligomers which are then reacted with carboxylic acid monomers such as acrylic acid to give radiation crosslinkable pressure sensitive adhesive compositions.

However, nothing in these publications has shown the advantages of using the reactions of the present invention with polar polymers, nor has there been any suggestion of the preparation of hydrophilic pressure sensitive adhesives through plasticization with humectants and crosslinking.

In another aspect of the invention, novel pressure sensitive adhesives are obtained by exposing a mixture of a polar polymer functionalized with pendant free-radically polymerizable moieties and a plasticizer compatible with this polymer to a source of free radicals. In order for the resulting swollen network to possess a degree of pressure sensitive tack, the functionalized polar polymer should be present in an amount of about 5 to 50 weight percent with plasticizer being present in amount of about 95 to 50 weight percent.

If too little functionalized polar polymer is present, difficulty could be encountered in crosslinking the composition to obtain adequate cohesive strength. If too much functionalized polar polymer is present, the resulting network could have too high a modulus to possess adhesive properties.

Similarly, the degree of functionalization of the polar polymer can impact adhesive properties since it determines the crosslink density of the resulting network. If there are too many pendant free-radically polymerizable moieties, a brittle, tack free elastomer could result. If there are too few pendant free-radically polymerizable moieties, cohesive strength could be compromised. Polar polymers which are functionalized with pendant moieties along the backbone with an average of about 2,500 to 25,000 g/mole molecular weight between pendant moieties crosslink to give materials with an appropriate balance of tack and cohesive strength.

For the optimum balance of adhesive properties, preferably the amount of functionalized polar polymer present in the composition ranges from about 10 to about 25 weight percent and the molecular weight between pendant functionality ranges from about 8,000 to about 20,000 g/mole.

In another aspect of the present invention, the pressure sensitive adhesive composition can be used in a medical device requiring pressure sensitive adhesiveness to mammalian skin. Often, additional ingredients are included, and the pressure sensitive adhesive must be compatible with them.

For example, pressure sensitive adhesives used in transdermal drug delivery devices may also serve as a reservoir for the drug. Pressure sensitive adhesives used in wound dressings may require high moisture vapor transmission rates to prevent skin maceration and aid healing. Pressure sensitive adhesives used in biomedical electrodes may need to be ionically-conductive.

Another advantage of the pressure sensitive adhesive compositions of the present invention is their ability to be used in biomedical electrodes, wound dressings, and transdermal drug delivery devices.

For a greater appreciation of the invention, embodiments of the invention are described with reference to the following drawings.

EMBODIMENTS OF THE PRESENT INVENTION

Polar Polymer

Nonlimiting examples of useful carboxy-functional polar polymers include:

(1) homopolymers of acrylic acid, carboxyethyl acrylate, and methacrylic acid, (including those that are partially or fully neutralized as the ammonium, lithium, sodium, or potassium carboxylate);

(2) copolymers of acrylic acid, carboxyethyl acrylate, itaconic acid, fumaric acid, maleic acid, or methacrylic acid (and their salts) with other polar monomers including:
  (a) ammonium or metal salts of sulfonic or phosphonic acids (e.g., 2-sulfoethyl methacrylate, 3-sulfopropyl acrylate, 2-acrylamido-2-methylpropane sulfonic acid, styrene sulfonic acid, vinyl benzyl phosphonic acid);
  (b) amides (e.g., acrylamide, methacrylamide, N,N-dimethyl acrylamide, and N-vinyl pyrrolidone);
  (c) ethers (e.g., 2-ethoxyethyl acrylate and 2-methoxyethyl methacrylate);
  (d) monomers having hydroxyl functionality (e.g., 2-hydroxyethyl acrylate, 2-hydroxyethyl methacrylate, and dihydroxy propylacrylate); or
  (e) ammonium functionality derived from reaction of amine containing monomers (e.g., N,N-dimethyl aminoethyl methacrylate and vinyl pyridine) with alkylating agents (3) cellulosics such as carboxy methyl cellulose; and (4) derivatized materials such as the acid grafted poly (ethylene oxides) sold by Union Carbide Corporation under the UCARMOD tradename.

One skilled in the art will recognize that moderate levels of non-polar monomers, such as alkyl acrylates and methacrylates of from 4 to 16 carbon atoms or vinyl and isopropenyl carboxylates, can be useful in these copolymers to impart cohesive strength and limit moisture sensitivity without having a detrimental effect on the compatibility of the copolymer with polar plasticizer.

Many of these polymers are commercially available or can be synthesized by standard free-radical solution polymerization methods as outlined in Sorenson and Campbell, *Preparative Methods of Polymer Chemistry*, Second Edition, John Wiley & Sons, 1968.

Homopolymers of acrylic acid and methacrylic acid and their alkali metal salts and copolymers of acrylic acid and its alkali salts with acrylamide or N-vinyl pyrrolidone are currently preferred because they are commercially available and give acceptable performance.

Free Radically Polymerizable Moieties

The carboxy-functional polar polymers described above are functionalized with pendant free-radically polymerizable moieties by reaction with an epoxy-functional acrylate or methacrylate monomer.

Nonlimiting examples of such monomers include glycidyl acrylate and glycidyl methacrylate. Glycidyl methacrylate is preferred because it gives adequate reactivity without causing gelation problems during functionalization.

Generally the carboxy functionality is present in large molar excess, ensuring that all the epoxy functionality is consumed in the reaction. Desirably for acrylic acid homopolymer, the molar ratio of carboxy functionality to epoxy functionality ranges from about 33/1 to about 330/1 to provide polar polymers which are functionalized with pendant moieties along the backbone with an average of about 2,500 to 25,000 g/mole molecular weight between pendant moieties. Preferably with acrylic acid homopolymer, the molar ratio of carboxy functionality to epoxy functionality ranges from about 100/1 to about 270/1 to provide the molecular weight between pendant functionality ranging from about 8,000 to about 20,000 g/mole.

Plasticizer

The plasticizer serves to increase the compliance of the crosslinked polymer composition to provide adhesive properties and conformability. The plasticizer also serves to modify the tack or thumb appeal of the crosslinked polymer composition. The plasticizer can also also serve as a solvent to dissolve other additives including initiators, electrolytes, and pharmacologically active components.

Using water alone as the plasticizer yields compositions with poor to moderate tack which are prone to rapid loss of moisture and a concomitant change into a leathery or glassy material when exposed to ambient conditions.

Hence useful plasticizers are those selected from the group consisting of alcohols, mixtures of alcohols, and mixtures of water and alcohols such that the mixture of plasticizer and carboxy-functional polymer is liquid in the uncrosslinked state and displays pressure sensitive tack in the crosslinked state.

Nonlimiting alcohols for the polar polymers described above include glycerin, propylene glycol, dipropylene glycol, sorbitol, 1,3-butanediol, 1,4-butanediol, trimethylol propane, and ethylene glycol and derivatives given by:

$$MO(CH_2CH_2O)_mH$$

wherein

M is selected from the group consisting of hydrogen and $C_1$ through $C_6$ alkyl, and m is an integer of about 1 to about 25.

Optional Surfactants

Anionic, cationic, nonionic or amphoteric surfactants can optionally be used in amounts ranging from about 10 to about 80 weight percent of the crosslinked composition and preferably from about 20 to about 50 weight percent of the crosslinked composition.

The use of such surfactants improves the adhesion of the pressure sensitive adhesive electrodes to oily mammalian skin by giving the adhesive lipophilic properties. By incorporating the surfactants into the adhesive composition, the compatibility between the adhesive and the oily mammalian skin is improved.

Suitable anionic compatible surfactants include alkyl benzene sulfonates, alkyl sulfonates, olefin sulfonates, alkyl ethersulfonates, glycerol ethersulfonates, α-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide (ether)sulfates, sulfosuccinates, sulfosuccinamates, sulfotriglycerides, amide soaps, ether carboxylic acids, isethionates, sarcosinates, taurides, alkyl oligoglycoside sulfates and alkyl (ether)phosphates.

Suitable nonionic compatible surfactants include fatty alcohol polyglycolethers, alkyl phenylpolyglycolethers, fatty acid polyglycolesters, fatty acid amide polyglycolethers, fatty amine polyglycolethers, alkoxylated triglycerides, alk(en)yl oligoglycosides, fatty acid glucamides, polyol fatty acid esters, sugar esters, sorbitol esters and sorbitol ester ethoxylates and polysorbates.

Suitable cationic compatible surfactants include quaternary ammonium compounds and quaternized difatty acid trialkanol amine esters.

Suitable amphoteric compatible surfactants include alkyl betaines, alkyl amidobetaines, amino propionates, amino glycinates, imidazolinium betaines and sulfobetaines.

Preferred compatible surfactants may be selected from nonionic surfactants having an HLB-value of 10 to 17. Fatty alcohol polyglycolethers, sorbitol fatty acid esters, and sorbitol fatty ester ethoxylates in this HLB range are particularly preferred. As is known to those skilled in the art, the HLB-value is an acronym for the hydrophilic-lipophilic balance and indicates the extent to which a given surfactant will behave as an oil-soluble vs. a water-soluble type of emulsifier as described in Chapter 20 of *Surface Active Agents and Detergents*, Volume II, Anthony M. Schwartz, James W. Perry, and Julian Berch, Robert E. Krieger Publishing Co., Huntington, New York, 1977. HLB-values in this range help assure that the surfactant is soluble in the adhesive formulation and also have high enough hydrocarbon content to impart desired oil absorbancy at lower usage.

Optional Processing Additives

Additives can also be incorporated into the composition including low levels of copolymerizable vinyl monomers, non-functionalized compatible polymers, and electrolytes.

Low levels of copolymerizable vinyl monomers, particularly those miscible in the reactive polymer/plasticizer mixture, can serve to accelerate the rate of crosslinking. Preferred copolymerizable monomers include acrylic acid and methacrylic acid and their ammonium and alkali metal salts, N-vinyl pyrrolidone, acrylamide, 2-acrylamido-2-methyl propane sulfonic acid and its ammonium and alkali metal salts, hydroxyethyl acrylate, hydroxyethyl methacrylate, 2-ethoxyethyl acrylate, 2-ethoxyethyl methacrylate, and 2-(2-ethoxyethoxy)ethyl acrylate. When utilized, the amount of copolymerizable vinyl monomer preferably comprises from about 2 to about 15 weight percent of the total adhesive composition.

Addition of non-functionalized compatible polymers is contemplated as a means of enhancing the viscosity of the precursor prior to cure to impart better coatability for, for example, pattern coating of the adhesive. Suitable polymers include those that are hydrophilic and compatible in the reactive polymer/plasticizer mixture including moderate and high molecular weight poly(ethylene oxide), poly(acrylic acid), poly(N-vinyl pyrrolidone), poly(vinyl alcohol), and poly(acrylamide).

Biocompatible and/or Therapeutic and/or Ionically-Conductive Additives

Depending upon the use of the hydrophilic, pressure sensitive adhesive of the present invention, various biocompatible and/or therapeutic and/or ionically-conductive materials can be included in the adhesive.

For example, adhesives of the present invention can be used as conductive adhesive in a biomedical electrode with the addition of an ionically-conductive electrolyte to the adhesive. Nonlimiting examples of electrolyte include ionic salts dissolved in the adhesive to provide ionic conductivity and can include magnesium acetate, magnesium sulfate, sodium acetate, sodium chloride, lithium chloride, lithium perchlorate, sodium citrate, and preferably potassium chloride to enhance ionic conductivity of the hydrophilic pressure sensitive adhesive.

Alternatively, a redox couple such as a mixture of ferric and ferrous salts such as sulfates and gluconates can be added.

The amounts of these ionic salts present in adhesives of the present invention are relatively small, from about 0.5 to 7 percent by weight of the adhesive, and preferably about 2 to 5 weight percent. When a redox couple is used, the biomedical electrode can recover from an overload potential. U.S. Pat. No. 4,846,185 (Carim) discloses a redox couple totalling not more than about 20 percent by weight of the adhesive.

Hydrophilic, pressure sensitive adhesives of the present invention can also be used in the delivery of pharmaceuticals to or through mammalian skin, such as topical or transdermal drug delivery systems. The pharmaceutical or other active ingredient can be compounded with the adhesive after polymerization, minimizing any possible deleterious interaction of the pharmaceutical or active ingredient with the crosslinking process.

A type of therapeutic procedure both involving application of electrical current to skin of a patient and a pharmaceutical is iontophoresis, which delivers an iontophoretically active pharmaceutical to or through mammalian skin with aid of an electrical current.

The hydrophilic, pressure sensitive adhesive can also be used in therapeutic mammalian skin coverings, such as dressings, wound closure materials, tapes, and the like. Preferably, for mammalian skin covering uses, other biologically active materials can be added to the adhesive of the present invention after crosslinking without deleteriously affecting the biologically active material. Nonlimiting examples of such other biologically active materials include broad spectrum antimicrobial agents where it is desired to reduce bacteria levels to minimize infection risk or treat the effects of infections at the skin or skin openings of a mammalian patient. Broad spectrum antimicrobial agents are disclosed in U.S. Pat. No. 4,310,509, which disclosure is incorporated by reference. Nonlimiting examples of other antimicrobial agents include parachlorometaxylenol; triclosan; chlorhexidine and its salts such as chlorhexidine acetate and chlorhexidine gluconate; iodine; iodophors; poly-N-vinyl pyrrolidone-iodophors; silver oxide, silver and its salts, antibiotics (e.g., neomycin, bacitracin, and polymyxin B). Antimicrobial agents can be included in the adhesive after crosslinking in a weight from about 0.01 percent to about 10 percent by weight of the total adhesive.

Other biocompatible and/or therapeutic materials can be added to the adhesive such as compounds to buffer the pH of the adhesive to provide a non-irritating pH for use with sensitive mammalian skin tissue or to otherwise maximize antimicrobial activity. Also, penetration enhancing agents or excipients can be added to the adhesive when the pharmaceutical or other active agent for topical or transdermal delivery so requires.

Method of Preparation

The reaction of the carboxy-functional polar polymer with the epoxy acrylate or methacrylate can be conducted in the presence of some or all of the plasticizer. As detailed in the Examples below, a typical preparation involves heating a solution of the carboxy-functional polymer at a time and temperature sufficient to destroy the majority of residual thermal initiator prior to adding the epoxy acrylate. The solution is then sparged with oxygen and a low level of a free-radical inhibitor, such as 4-methoxyphenol ("MEHQ"), is introduced with stirring followed by the epoxy acrylate or methacrylate. The reaction is substantially complete within an hour at 60 to 80° C. and the resulting solution can be diluted further with plasticizer as required.

Crosslinking of the reactive polymer/plasticizer mixture is accomplished by exposing it to a source of free radicals. As one skilled in the art will recognize, free radicals can be generated by thermal, redox, or photochemical means or by exposure of the material to a source of actinic radiation.

Suitable thermal initiators include azo compounds, peroxides, and persulfates and when the latter two groups are used in combination with a reducing agent such ascorbic acid or a bisulfite compound and optionally, a catalytic amount of a transition metal salt such as iron or copper, redox generation of radicals may occur even at sub-ambient temperatures.

When visible or ultraviolet light is used for crosslinking a photoinitiator is included. Suitable photoinitiators include benzoin ethers, benzophenone and derivatives thereof, acyl phosphine oxides, acetophenone derivatives, camphorquinone, and the like. Suitable light sources to effect this crosslinking include medium pressure mercury lamps emitting light at a wavelength of about 365 nm and low intensity "black light" fluorescent bulbs emitting light at a wavelength of about 351 nm. Using either type of light source, light energy reaching the uncrosslinked composition should range from about 50 to about 1000 $mJ/cm^2$, and preferably about 300 $mJ/cm^2$ UV energy. Photoinitiator is generally used at a concentration of from about 0.05 to about 5 weight percent.

In the absence of initiator, exposure to actinic radiation such as electron beam irradiation or a cobalt 60 gamma source will also generate free radicals under conditions known to one skilled in the art.

The reactive polymer/plasticizer mixture can be coated via any of a variety of conventional coating methods, such as roll coating, knife coating, or curtain coating, or can be extruded. The low viscosity allows for injection into cavities of, for example, a monitoring ECG electrode, or pattern coating of the adhesive precursor is possible, particularly with viscosity enhancement.

The precursor can be coated directly on to the flexible substrate of choice including metal foils and metallized polymeric films for conductive adhesives, or can be coated and crosslinked on a release liner to yield a transfer adhesive. In this latter application it is desirable to embed a tissue paper or non-woven fabric scrim, such as a 0.1 mm Cerex™ material from Monsanto Chemical Company in the precursor to allow for ease of handling.

Crosslinking is best accomplished with the exclusion of oxygen, either in an inert atmosphere such as nitrogen or argon, or by covering the precursor with a non-oxygen permeable film. When crosslinking is done photochemically, this film cover should be substantially transparent to the wavelengths of interest.

Usefulness of the Invention

Adhesive compositions of the present invention can be used in a variety of applications where pressure sensitive adhesives are industrially or commercially applied in the manufacture of tapes, adhesive substrates, and the like. Preferably, adhesive compositions of the present invention can be used in the field of health care where adhesive requirements are particularly stringent and efficient manufacturing is desired.

Because mammalian skin is a particularly difficult surface to identify and control acceptable adhesive properties, the adhesive composition of the present invention is particularly suitable for use in mammalian skin covering applications such as biocompatible medical adhesives such as for receipt or delivery of electrical signals at or through mammalian skin, delivery of pharmaceuticals or active agents to or through mammalian skin, or treatment of mammalian skin or mammalian skin openings against the possibilities of infection.

Biomedical Electrodes

Biomedical electrodes employing adhesive compositions of the present invention having electrolyte contained therein are useful for diagnostic (including monitoring) and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

Figure 1:
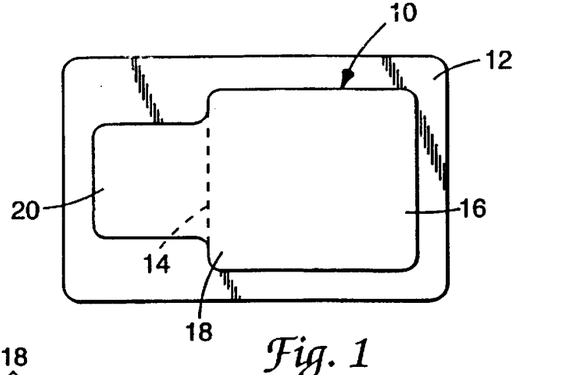
FIG. 1 is a top plan view of a biomedical electrode containing an adhesive composition of the present invention, used for diagnosis or monitoring of heart conditions of a mammalian patient.
Figure 2:
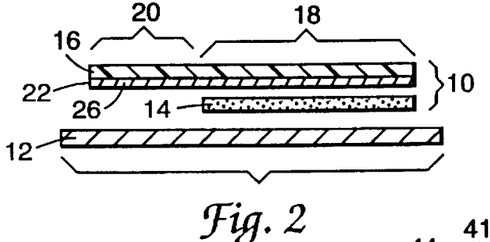
FIG. 2 is a cross-sectional view of the biomedical electrode of FIG. 1.

FIGS. 1 and 2 show either a disposable diagnostic electrocardiogram (ECG or EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred for conductor member 16 are polyester films commercially available as Scotchpak™ brand film from Minnesota Mining and Manufacturing Company of St. Paul, Minn. or "Melinex" 505-300, 329, or 339 brand film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" material from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3 M Company as "Blenderm" tape can be employed for this purpose.

Alternatively, conductor member can be a multi-layered construction of a nonconductive, flexible polymeric film having a sulfur-reactive surface, a metallic layer deposited on and interacting with the surface and an optional metallic halide layer, according to the disclosure of PCT Publication WO 94/026950, the disclosure of which is incorporated by reference herein. The conductive interface portion 18 of member 16 comprises a metallic layer deposited on a sulfur-reactive surface on at least the side of polymeric film substrate facing field 14 of the conductive medium and the optional metallic halide layer coated on the metallic layer and contacting field 14. Because depolarizing is not needed for the mechanical and electrical contact with electrical equipment, the optional metallic halide layer does not need to extend to tab portion 20.

Alternatively, conductor member 16 can be a multi-layered construction of a nonconductive, flexible polymeric film, an electrically conductive layer, and a thin, conformable depolarizing layer of inorganic oxide, preferably manganese dioxide. Alternatively, conductor member 16 is a multi-layered construction of film with electrically conductive and depolarizing layers blended together. Both of these alternative embodiments can be constructed according to the disclosure of PCT International Patent Publication WO 95/20350, the disclosure of which is incorporated by reference herein. The conductive interface portion of member comprises an electrically conductive layer coated on at least the side of polymeric film facing field 14 of conductive medium and the thin, depolarizing layer coated on the electrically conductive layer and contacting field 14. Because depolarizing is not needed for the mechanical and electrical contact with electrical equipment, the depolarizing layer does not need to extend to tab portion 20.

Non-limiting examples of biomedical electrodes which can use adhesive compositions of the present invention, either as conductive or non-conductive adhesive fields include electrodes disclosed in U.S. Pat. Nos. 4,524,087; 4,539,996; 4,554,924; 4,848,353 (all Engel); 4,846,185 (Carim); 4,771,783 (Roberts); 4,715,382 (Strand); 5,012,810 (Strand et al.); and 5,133,356 (Bryan et al.), the disclosures of which are incorporated by reference herein.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, an adhesive composition of the present invention, containing an electrolyte, can reside as a field of conductive adhesive on a biomedical electrode for diagnostic (including monitoring), therapeutic, or electrosurgical purposes.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The adhesive of the present invention can be used as the ionically conductive medium in any of the embodiments shown therein. Preferably, the adhesive of the present invention is used as the field of conductive adhesive in the biomedical electrode of the embodiment shown in FIGS. 2, 3, and 4 of U.S. Pat. No. 5,012,810.

Figure 3:
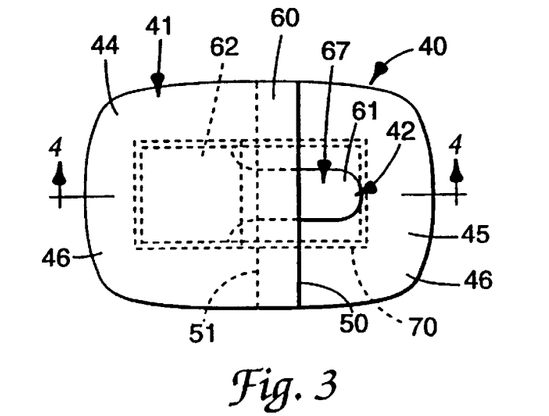
FIG. 3 is a top plan view of a monitoring biomedical electrode containing an adhesive composition of the present invention, used for longer term diagnosis or monitoring of heart conditions.
Figure 4:
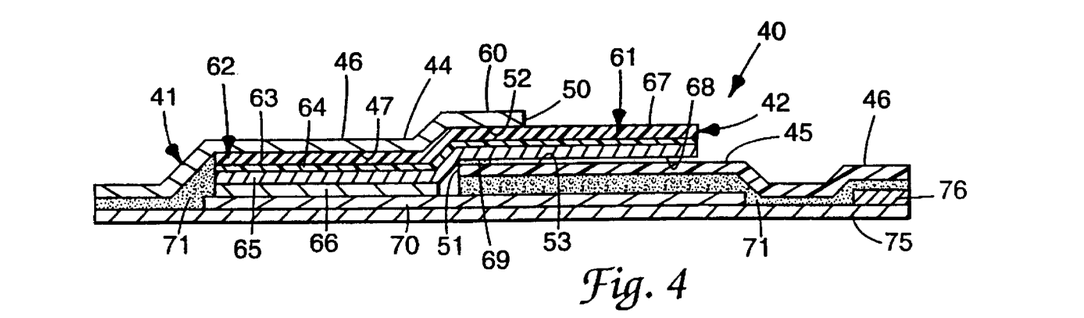
FIG. 4 is a cross-sectional view of the monitoring biomedical electrode of FIG. 3.

FIGS. 3 and 4 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 3, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment, conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of PCT Patent Publication WO 94/-26950.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2 in order to enhance mechanical contact.

In general, electrode 40 is constructed such that tab portion 61 of conductor member 42 projects through seam 60 and over a portion of surface or side 46. As a result, as seen in FIGS. 3 and 4 pad portion 62 of conductor member 42 is positioned on one side 46 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 4, lower surface 68 of tab portion 61 is shown adhered in position to section 45, by means of double-stick tape strip 69. That is, adhesion in FIG. 4 between the tab portion 61 and section 45 is by means of adhesive 69 underneath tab portion 61.

In FIG. 4, a field 70 of conductive adhesive of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon.

In FIG. 4, a layer of release liner 75 is shown positioned against that side of electrode 40 which has optional skin adhesive 71, conductive adhesive 70 and pad portion 62 thereon. Optionally as shown in FIG. 4, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, non-woven pads, especially polyester non-wovens, various types of paper, and transparent films. Nonlimiting examples of transparent films include polyester film such as a "Melinex" polyester film commercially available from ICI Americas, Hopewell, Va. having a thickness of 0.05 mm and a surgical tape commercially available from 3 M Company as "Transpore" unembossed tape.

The most preferred materials are non-woven pads made from melt blown polyurethane fiber, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.54.5 cm by 5.5–10 cm will be quite suitable for typical foreseen applications.

It will also be understood that a variety of materials may be utilized as the skin adhesive. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732, 808; 4,917,928; 4,917,929; and European Patent Publication 0 05 1 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

It will be understood that the dimensions of the various layers, and their conformation during association, are shown somewhat exaggerated in FIG. 4, to facilitate an understanding of the construction. In general, an overall substantially flat appearance with only a very minor "s" type bend in the conductive member 42 is accommodated by the arrangement, despite the multi-layered construction of member 42.

Figure 5:
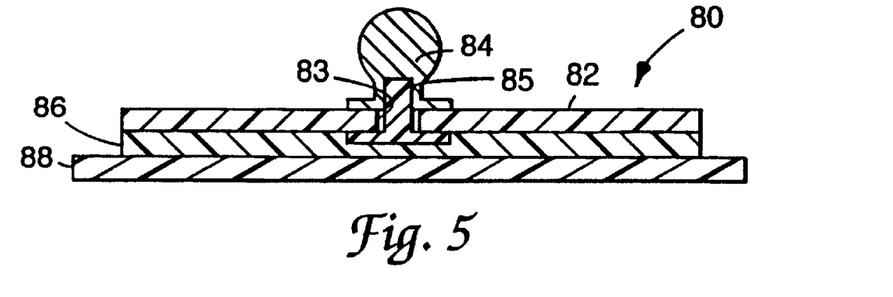
FIG. 5 is a cross-sectional view of another monitoring biomedical electrode containing an adhesive compositon of the present invention and a stud connector.

Another biomedical electrode construction is shown in FIG. 5 in cross-section. Electrode 80 has a nonconductive backing 82 having an opening 83 covered by snap 84 though which stud or eyelet 85 protrudes. The snap 84 is secured to eyelet 85 to provide a point of electrical connection to electrical instrumentation. Covering eyelet 84 and backing 82 is a field 86 of the adhesive of the present invention. A release liner 88 protects the PSA field 86 prior to use. Backing 82 can be made of the same or similar materials as insulator construction 41. Eyelet 85 can be a plastic, metallic plated eyelet (such as an ABS plastic eyelet silver-plated and chlorided and commercially available from Micron Products of Fitchburg, Mass.). Snap 84 can be a metallic snap (such as stainless steel eyelet No. 304 commercially available from Eyelets for Industry of Thomason, Conn.).

Other examples of biomedical electrodes which can use the present invention as a conductive adhesive include electrodes disclosed in U.S. Pat. No. 4,527,087; 4,539,996; 4,554,924; 4,848,353 (all Engel); 4,846,185 (Carim); 4,771,783 (Roberts); 4,715,382 (Strand); 5,133,356 (Bryan et al.), the disclosures of which are incorporated by reference herein. Methods of making such electrodes are disclosed in such patents, except that adhesive of the present invention can be substituted for the field of conductive adhesive. Among these various electrode constructions is an electrode construction particularly preferred as that shown in FIGS. 4 and 5 of U.S. Pat. No. 4,848,353 (Engel) in which the electrically conductive adhesive 36 is replaced by the adhesive of the present invention, .

When used for diagnostic EKG procedures, electrodes shown in FIGS. 1 and 2 or those electrodes shown in U.S. Pat. No. 4,539,996 are preferred. When used for monitoring electrocardiogram (ECG) procedures, electrodes shown in FIGS. 3 and 4 and those disclosed in U.S. Pat. Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto.

Medical Skin Coverings

Medical skin coverings employing adhesive compositions of the present invention, optionally having antimicrobial and other biologically active agents contained therein, are useful for treatment of mammalian skin or mammalian skin openings, preferably against the possibility of infection and also for the transmission of moisture vapor and exudate from skin.

Figure 6:
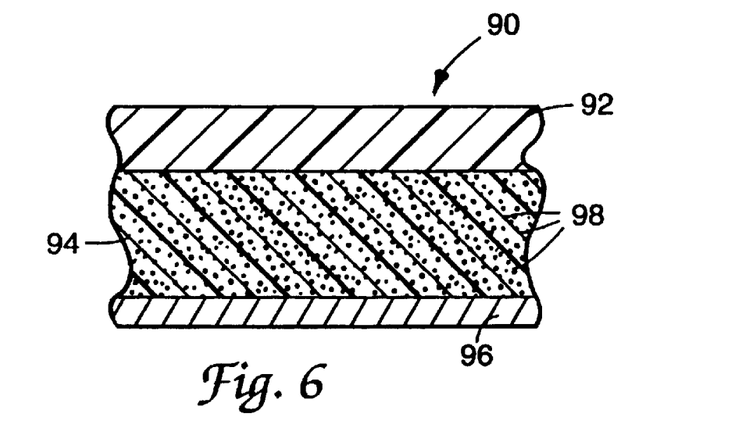
FIG. 6 is a sectional view of a medical mammalian skin covering containing adhesive composition of the present invention.

FIG. 6 shows a sectional view of a medical skin covering 90 having a backing material 92, a layer 94 of adhesive of the present invention coated on backing material 92, and protected until use by a release liner 96. Preferably, antimicrobial 98 is contained in layer 94 by adding agent 98 prior to coating on backing material 92. Alternatively, layer 94 can be used as a caulkable sealant according to U.S. Pat. No. 4,931,282 (Asmus et al.), the disclosure of which is incorporated by reference herein.

For use, the release liner 96 is removed and the layer 94 of adhesive of the present invention can be applied to the skin of the patient as a part of a medical tape, a wound dressing, a bandage of general medicinal utility, or other medical device having water absorbing properties.

The adhesive layer 94 may be coated on a layer of backing material 92 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel$^R$ 4056" and "Hytrel$^R$ 3548" branded polyester elastomers available from E. I. DuPont de Nemours and Company of Wilmington, Del., "Estane" branded polyurethanes available from B. F. Goodrich of Cleveland, Ohio or "Q-thane" branded polyurethanes available from K. J. Quinn & Co. of Maiden, Mass.

The layer 94 of adhesive of the invention combined with a layer 92 of suitable backing material can be used as a dressing.

Adhesive compositions of the present invention can be used as discrete gel particles dispersed in a continuous pressure-sensitive adhesive matrix to form a two phase composite useful in medical applications, as described in U.S. Pat. No. 5,270,358, the disclosure of which is incorporated by reference herein.

The adhesive layer 94 can be coated on the backing layer 92 by a variety of processes, including, direct coating, lamination, and hot lamination. The release liner 96 can thereafter be applied using direct coating, lamination, and hot lamination.

The methods of lamination and hot lamination involve the application of pressure, or heat and pressure, respectively, on the layer of adhesive layer 94 to the backing material layer 92. The temperature for hot lamination ranges from about 50° C. to about 250° C., and the pressures applied to both lamination and hot lamination range from 0.1 Kg/cm$^2$ to about 50 Kg/cm$^2$.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 7:
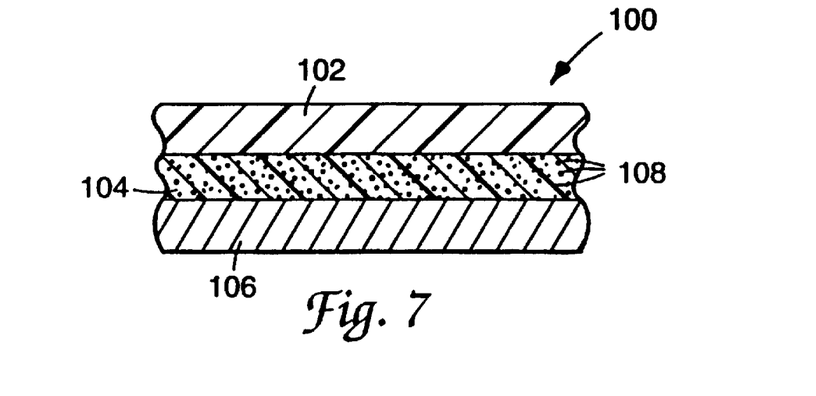
FIG. 7 is a sectional view of a pharmaceutical delivery device containing an adhesive composition of the present invention.

FIG. 7 shows a sectional view of a transdermal or topical drug delivery device 100 having a backing layer 102, a layer 104 containing adhesive of the present invention coated thereon and protected by a release liner 106. Other layers can be present between layer 102 and layer 104 to house pharmaceuticals or other therapeutic agents. Otherwise, as shown in FIG. 7, pharmaceutical and other agents 108 are dispersed in adhesive layer 104.

The backing layer 102 can be any backing material known to those skilled in the art and useful for drug delivery devices. Non-limiting examples of such backing materials are polyethylene, ethylene-vinyl acetate copolymer, polyethylene-aluminum-polyethylene composites, and ScotchPak™ brand backings commercially available from Minnesota Mining and Manufacturing Company of St. Paul, Minn.

The release liner 106 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand ScotchPak™ release liners.

The therapeutic agent 108 can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

The method of manufacturing a transdermal delivery device depends on its construction.

The drug delivery device 100 shown in FIG. 7 can be prepared using the following general method. A solution is prepared by dissolving the therapeutic agent 108 and such optional excipients as are desired in a suitable solvent and mixed into the precursor prior to forming the composition, during the formation of the composition, or directly into the already formed composition. The resulting loaded adhesive composition is coated on the backing layer 102. A release liner 106 is applied to cover loaded adhesive layer 104.

Other aspects of the present invention are identified in the following examples.

EXAMPLES

Assessment of Tack

The adhesive composition is evaluated for initial tack immediately following crosslinking. In this test, firm pressure is applied to the sample with a thumb and the thumb removed. Tack is qualitatively assessed and assigned a value of 1 through 5 where 1=very firm, tack free; 2=moderately firm, acceptable tack; 3=moderately soft, good tack, no residue; 4=moderately soft, acceptable tack, no residue; 5=very soft, residue transferred to thumb on removal. On this scale values of 2, 3, and 4 represent adhesives with a desirable balance of sufficient compliance to possess tack and sufficient integrity to possess cohesive strength.

Examples 1 through 5 Comparative Example 1

Functionalization of Callaway 4608 Polymer Solution with Glycidyl Methacrylate

Into a one liter 3-necked flask equipped with mechanical stirrer, thermometer and reflux condenser was charged 900 g Callaway® 4608 polymer solution, a 22% solids aqueous solution of a moderate molecular weight 92/8 copolymer of acrylamide and acrylic acid commercially available from Callaway Chemical Company, Columbus, Ga. This solution (with 198 g polymer contained) was heated with a heating mantel to 95° C. over the course of 40 minutes while stirring under an air atmosphere. This was done to destroy residual thermal initiator and prevent gelation during the next step. Heating was then discontinued and 10 minutes later 200 ppm (0.18 g) 4-methoxyphenol (MEHQ) was charged as an inhibitor followed by 1.88 g (13.2 mmole) glycidyl methacrylate (GMA). This results in a calculated level of functionalization of one GMA group every 15,000 molecular weight along the copolymer backbone.

This homogeneous solution was stirred for an additional 60 minutes (during which time in the absence external heating the temperature had dropped to 84° C.) then 450 g was transferred out of the flask. To the remaining 450 g was charged 0.45 g (3.2 mmole) additional GMA, the mixture stirred well and also transferred out of the flask allowing to cool to room temperature and sit overnight. This additional charge of GMA results in a calculated level of functionalization of one GMA group every 10,000 molecular weight along the copolymer backbone for this half of the polymer solution.

After sitting overnight a 50 g portion of each of the 15,000 and 10,000 mw functionalized materials were formulated with 49 g of glycerin and 1 g of 2-hydroxy-2-methyl-1-phenyl-propan-1-one, a photoinitiator available from Ciba-Giegy Corporation, Hawthorne, N.Y. under the tradename Darocur® 1173.

The resulting 11/39/49/1 functionalized polymer/water/ glycerin/photoinitiator solutions were coated at a thickness of about 0.6 mm between 40 micrometer (1.5 mil) siliconized polyester liners and passed under a single 15 cm F300 H lamp, four passes at 15 meters per minute using an LC-6 Benchtop conveyer. Both the F300 lamp system and the LC-6 conveyer were obtained from Fusion Systems Corporation, Rockville, Md. Under these conditions each pass exposed the precursor solutions to 80 mJ/cm$^2$ UV energy giving a total dose of 320 mJ/cm$^2$.

The adhesive resulting from the precursor functionalized every 15,000 molecular weight (Example 1) was moderately soft with good tack and no residue (corresponding to a tack value of 3 as detailed above).

The 10,000 molecular weight material (Example 2) was moderately firm with acceptable tack (corresponding to a tack value of 2). The 22% solids aqueous solution of copolymer functionalized every 10,000 molecular weight was formulated further with glycerin in 1 to 1, 2 to 3, 3 to 7, and 1 to 4 ratios again adding 1% photoinitiator. These formulations were cured as described above using the Fusion system at 9 meters per minute for two or three passes (as noted in Table below), each pass exposing the precursor solutions to 130 mJ/cm$^2$ UV energy. The tack for the resulting adhesives, which varied in percent solids contents, was evaluated for initial tack immediately following curing as described above. Specifics of the formulations, cure, and tack assessment are shown in the Table 1 below.

TABLE 1

| Example | 10,000 mw copolymer/ water/glycerin/Darocur | Cure (# of passes) | Tack |
|---|---|---|---|
| 3 | 11/39/49/1 | 2 | 2 |
| 4 | 9/31/59/1 | 2 | 3 |
| 5 | 7/23/69/1 | 3 | 4 |
| Comparative 1 | 4/16/79/1 | 3 | 5 |

These results show that as the level of solids is reduced below about 5 weight percent adequate crosslinking cannot be achieved under these conditions.

Examples 6 through 10, Comparative Example 2

Functionalization of Sokalan PA 70PN Polymer Solution with Glycidyl Methacrylate.

Into a 500 mL 3-necked flask equipped with mechanical stirrer, thermometer and reflux condenser was charged 200 g Sokalan® PA 70PN polymer solution, a 30% solids aqueous solution of a 70,000 molecular weight partially neutralized acrylic acid homopolymer commercially available from BASF Corporation, Parsippany, N.J. This solution (with 60 g polymer contained) was heated with a heating mantel to 90° C. over the course of 30 minutes while stirring under an air atmosphere. This was done to destroy residual thermal initiator and prevent gelation during the next step. 200 ppm (0.04 g) 4-methoxyphenol (MEHQ) was charged as an inhibitor followed by 0.45 g (3.2 mmole) glycidyl methacrylate (GMA). This results in a calculated level of functionalization of one GMA group every 19,000 molecular weight along the polymer backbone.

This homogeneous solution was stirred for 35 minutes, a sample was removed and cure was checked by adding a drop of Darocur 1173, mixing, and placing a portion between 40 micrometer siliconized polyester liners. The resulting laminate was exposed to a bank of six Sylvania 15 watt F15T8 350 black light bulbs at a distance of 15 cm for 4 minutes giving a total dose of 250 mJ/sq. cm. The top inner was removed from the cured material and the tack assessed. The material cured under these conditions to a very soft low tack adhesive. The material was further functionalized by charging 0.12 g (0.8 mmole) additional GMA. This additional charge of GMA results in a calculated level of functionalization of one GMA group every 15,000 molecular weight along the polymer backbone.

After stirring 1 hour at 90° C., 100 g was transferred out of the flask. To the remaining 100 g was charged 0.13 g (0.9 mmole) additional GMA, the mixture stirred an additional 75 minutes at 90° and also transferred out of the flask allowing to cool to room temperature and sit overnight. This final charge of GMA results in a calculated level of functionalization of one GMA group every 10,000 molecular weight along the copolymer backbone for this half of the polymer solution. After sitting overnight portions of each of the 15,000 and 10,000 mw materials were formulated with glycerin and one drop Darocur® 1173 photoinitiator. Materials were cured between 40 micrometer siliconized polyester liners under low intensity UV lights as described above. Specifics of the formulations and tack assessment are shown in the Table 2 below:

TABLE 2

| Example | Functionalization | polymer/water/glycerin | Tack |
|---|---|---|---|
| 6 | 15,000 | 22.5/52.5/25 | 2 |
| 7 | 15,000 | 15/35/50 | 3 |
| Comparative 2 | 15,000 | 7.5/17.5/75 | 5 |
| 8 | 10,000 | 22.5/52.5/25 | 2 |
| 9 | 10,000 | 15/35/50 | 2 |
| 10 | 10,000 | 7.5/17.5/75 | 4 |

These results show that the tack of the adhesive is related to both the level of functionalization and the amount of functionalized polymer present.

Example 11

Functionalization of Narlex PPE 1177 Polymer Solution with Glycidyl Methacrylate.

Into a 250 mL 3-necked round bottom flask equipped with mechanical stirrer, thermometer and reflux condenser was charged 25 g glycerin and 50 g Narlex® PPE 1177 polymer solution, 25% solids aqueous solution of moderate molecular weight, partially neutralized (to pH 6) poly(acrylic acid) from National Starch, Bridgewater, N.J. After heating to 100° C. for 1 hour under air atmosphere to destroy any residual thermal initiator, the resulting solution (containing 12.5 g polymer) was cooled to 80° C. and 0.03 g (400 ppm) MEHQ and 0.18 g (1.3 mmole) GMA in 0.59 g ethanol was charged.

This results in a calculated level of functionalization of one GMA group every 10,000 molecular weight along the polymer backbone. After stirring 1 hour at 80° C., the mixture was cooled and 0.6 g Darocur 1173 added. The material was cured as described in Example 1 above, passing through the Fusion system one pass at 6 meters (20 feet) per minute (total dose of 200 mJ/sq cm). The resulting adhesive had a tack value of 3.

Examples 12 through 20

Polymerization and Functionalization of Poly (acrylic acid)

In the Presence of Mixed Sorbitol/Glycerin/Water Plasticizer

Into a one-liter three-neck flask was charged 12.0 g KCl, 27.66 g water, 86.82 g acrylic acid, 225.0 g glycerin, and 171.42 g 70% aq. sorbitol. The resulting mixture was stirred with an overhead mechanical stirrer while cooling in a water bath to 22° C. 77.1 g 50% aq NaOH (sufficient to neutralize 80% of the acrylic acid) was charged over 1½ minutes resulting in an exotherm to 58° C. After allowing to cool to 35° C. over 30 minutes, 2.4 g mercaptopropionic acid was charged as a chain transfer agent and the headspace purged with nitrogen for 5 minutes. 0.15 g potassium persulfate was dissolved in 5 g water and separately 0.05 g sodium bisulfite was dissolved in 5 g water.

These solutions were charged one after the other into the flask with stirring and served to initiate the polymerization of the acrylic acid. During this polymerization the contents of the air cooled flask exothermed to 47° C. over the course of fifteen minutes. The reaction was allowed to stir a further hour, then heated to 100° C. over the next 20 minutes using a heating mantle.

After holding at that temperature for 25 minutes to decompose residual initiator, heating was stopped, 0.18 g (300 ppm) MEHQ was charged to inhibit further free radical reactions, and air was bubbled through for five minutes.

A 50 g portion of the now 80° C. moderate viscosity solution was transferred into each of four jars. Glycidyl methacrylate was charged in the amounts shown below as was 0.10 g Darocur 1173, the resulting mixtures stirred well and allowed to cool, leaving in the dark overnight. Results for tack assessment on adhesives cured using the procedure described in Examples 6 through 10 are shown in Table 3 below as is the calculated level of functionalization for this 18% solids 80/20 sodium acrylate/acrylic acid copolymer.

TABLE 3

| Example | GMA charged | Level of functionalization | Tack |
|---|---|---|---|
| 12 | 0.07 g | 18,000 mw | 4 |
| 13 | 0.09 g | 14,000 mw | 3 |
| 14 | 0.14 g | 9,000 mw | 3 |
| 15 | 0.19 g | 7,000 mw | 2 |

In the Presence of a Mixed Glycerin/Nonionic Surfactant/Water Plasticizer

Into a one-liter three-neck flask was charged 12.0 g KCl, 27.66 g water, 86.82 g acrylic acid, 225.0 g glycerin, and 171.42 g 70% solids Glucopon® 225CS (a C8–10 alkylated polyglycoside (HLB 13.6) available from Henkel Corporation, Ambler, Pa.). The resulting mixture was stirred with an overhead mechanical stirrer while cooling in a water bath to 22° C. 77.1 g 50% aq NaOH (sufficient to neutralize 80% of the acrylic acid) was charged over 1½ minutes resulting in an exotherm to 58° C. After allowing to cool overnight to 25° C., 1.8 g mercaptopropionic acid was charged as a chain transfer agent and the headspace purged with nitrogen for 5 minutes. 0.15 g potassium persulfate was dissolved in 5 g water and separately 0.05 g sodium bisulfite was dissolved in 5 g water.

These solutions were charged one after the other into the flask with stirring and served to initiate the polymerization of the acrylic acid. During this polymerization the contents of the air cooled flask exothermed to 42° C. over the course of fifty minutes. The reaction was allowed to stir a further hour, then heated to 100° C. over the next 20 minutes using a heating mantle. After holding at that temperature for 90 minutes to decompose residual initiator, heating was stopped, 0.18 g (300 ppm) MEHQ was charged to inhibit further free radical reactions, and air was bubbled through for ten minutes.

A 50 g portion of the now 80° C. moderate viscosity solution was transferred into each of three jars. Glycidyl methacrylate was charged in the amounts shown below as was 0.10 g Darocur 1173, the resulting mixtures stirred well and allowed to cool, leaving in the dark overnight. Results for tack assessment on adhesives cured using the procedure described in Examples 6 through 10 are shown in Table 4 below as is the calculated level of functionalization for this 18% solids 80/20 sodium acrylate/acrylic acid copolymer.

TABLE 4

| Example | GMA charged | Level of functionalization | Tack |
| --- | --- | --- | --- |
| 16 | 0.13 g | 10,000 mw | 3 |
| 17 | 0.17 g | 7,500 mw | 3 |
| 18 | 0.26 g | 5,000 mw | 2 |

In the Presence of Mixed Glycerin/Water Plasticizer

Into a 500 mL three-neck flask was charged 50 g acrylic acid, 100 g deionized water, and 100 g glycerin. 28 g of a 10% aqueous solution of NaOH was charged (to neutralize 10% of the acrylic acid) followed by a solution of 0.25 g potassium persulfate in 10 g of water. The flask was purged with nitrogen for ten minutes, then heated to 60° C. with an oil bath while maintaining a slight flow of nitrogen. After 15 minutes an exotherm occurred (requiring removal of the oil bath) and the resulting viscous solution was held at 60° C. an additional 2 hours. Following this polymerization the mixture was heated to 100° C. for 1 hour to destroy residual initiator then the heat reduced to 80° C. while purging with air. 0.75 g (5.3 mmole) GMA and 0.15 g (500 ppm) MEHQ dissolved in 5 g ethanol was charged.

This results in a calculated level of functionalization of one GMA group every 9,700 molecular weight along the polymer backbone for this 18% solids 90/10 acrylic acid/sodium acrylate copolymer. After stirring 1 hour at 80° C., the mixture was cooled and 0.5 g Darocur 1173 added. The material was cured as described in Example 1 above, passing through the Fusion system one pass at 6 meters per minute (total dose of 200 mJ/sq cm). The resulting adhesive (Example 19) had a tack value of 3.

In the Presence of Mixed Glycerin/Nonionic Surfactant/Water Plasticizer

Into a 500 mL three-neck flask was charged 50 g acrylic acid, 100 g deionized water, and 75 g glycerin, and 50 g Arosurf 66 E 20, a PEG-20 Isostearyl ether (HLB 15.0) available from Sherex Chemical Company, Dublin, Ohio. 28 g of a 10% aqueous solution of NaOH was charged (to neutralize 10% of the acrylic acid) followed by a solution of 0.25 g potassium persulfate in 10 g of water. The flask was purged with nitrogen for ten minutes, then heated to 60° C. with an oil bath while maintaining a slight flow of nitrogen.

After 15 minutes an exotherm occurred (requiring removal of the oil bath) and the resulting viscous solution was held at 60° C. an additional 2 hours. Following this polymerization the mixture was heated to 100° C. for 1 hour to destroy residual initiator then the heat reduced to 80° C. while purging with air. 25 g additional water and 25 g additional glycerin were added to reduce viscosity. 0.75 g (5.3 mmole) GMA and 0.15 g (500 ppm) MEHQ dissolved in 5 g ethanol was charged.

This results in a calculated level of functionalization of one GMA group every 9,700 molecular weight along the polymer backbone for this 14% solids 90/10 acrylic acid/sodium acrylate copolymer. After stirring 1 hour at 80° C., the mixture was cooled and 0.5 g Darocur 1173 added. The material was cured as described in Example 1 above, passing through the Fusion system one pass at 6 meters per minute (total dose of 200 mJ/sq cm). The resulting adhesive (Example 20) had a tack value of 3.

For an appreciation of the scope of the present invention, the claims follows.

What is claimed is:

1. A hydrophilic pressure sensitive adhesive composition comprising:
    a crosslinked polar, hydrophilic polymer and sufficient humectant to render the composition pressure sensitive adhesive, wherein the crosslinked polymer is prepared from the reaction of hydrophilic, carboxy-functional polymers with epoxy-functional (meth)acrylates to become pendant polymerizable moieties, and wherein the hydrophilic, carboxy-functional polymers are functionalized with the pendant polymerizable moieties with an average of 2,500 to 25,000 g/mole molecular weight between the pendant polymerizable moieties along the backbone.

2. The composition of claim 1, wherein the crosslinked polymer comprises from 5 to 50 weight percent of the composition and wherein the humectant comprises from 95 to 50 weight percent of the composition.

3. The composition of claim 1, wherein the reactive polymer is selected from the group consisting of homopolymers of acrylic acid, carboxyethyl acrylate, methacrylic acid, and their salts; copolymers of acrylic acid, carboxyethyl acrylate, itaconic acid, fumaric acid, maleic acid, methacrylic acid, and their salts with other polar monomers; cellulosics; or acid grafted poly(ethylene oxides).

4. The composition of claim 2, wherein the polar monomers comprise ammonium or metal salts of sulfonic or phosphonic acids; amides; ethers; monomers having hydroxyl functionality; or ammonium functionality derived from reaction of amine containing monomers with alkylating agents.

5. The composition of claim 1, wherein the humectant comprises alcohols, mixtures of alcohols, or mixtures of water and alcohols such that the mixture of humectant and reactive polymer is liquid in the uncrosslinked state and displays pressure sensitive tack in the crosslinked state.

6. The composition of claim 1, wherein the composition further comprises surfactants, copolymerizable vinyl monomers, non-functionalized compatible polymers, electrolytes, or combinations thereof.

7. The composition of claim 1, wherein the composition further comprises ionic salts, pharmaceuticals, antimicrobial agents, or combinations thereof.

8. A method of preparing a crosslinked hydrophilic pressure sensitive adhesive composition, comprising the steps of:
   (a) reacting a carboxy-functional polar polymer with an epoxy (meth)acrylate to generate a functionalized polymer having pendant polymerizable moieties on the polymer with an average of 2,500 to 25,000 g/mole molecular weight between the pendant polymerizable moieties along the backbone;
   (b) free radically crosslinking the functionalized polymer in the presence of humectant to generate the crosslinked composition.

9. The process according to claim 8, wherein the free radical crosslinking is carried out in the presence of ultraviolet light using a photoinitiator.

10. A biomedical electrode, comprising:
    a field of adhesive conductive medium for contacting mammalian skin and a means for electrical communication for interfacing with the adhesive conductive medium and electrical diagnostic, therapeutic, or electrosurgical instrumentation, the adhesive conductive medium adhered to the means for electrical communication and comprising an adhesive composition according to claim 1.

11. The biomedical electrode according to claim 10, wherein the adhesive conductive medium further comprises a salt electrolyte present in an amount from 0.5 to 5 weight percent of the adhesive conductive medium.

12. The biomedical electrode according to claim 10, wherein the adhesive conductive medium further comprises a redox couple present in an amount of not more than 20 percent by weight of the adhesive conductive medium.

13. The biomedical electrode according to claim 10, wherein the means for electrical communication comprises a conductor member having an interface portion contacting the adhesive conductive medium and a tab portion available for mechanical and electrical contact with the electrical diagnostic, therapeutic, or electrosurgical instrumentation.

14. The biomedical electrode according to claim 10, wherein the means for electrical communication comprises a conductor member having an eyelet or snap connector contacting the adhesive conductive medium.

15. The biomedical electrode according to claim 10, wherein the means for electrical communication comprises a conductive member having a conductive layer coating at least on a side of the conductor member contacting the adhesive conductive medium.

16. The biomedical electrode according to claim 15, wherein said conductive layer coating is silver/silver chloride.

17. A mammalian skin covering comprising: an adhesive layer for contacting mammalian skin and backing layer, the adhesive layer adhered to the backing layer and comprising a pressure sensitive adhesive composition according to claim 1.

18. The mammalian skin covering according to claim 17, wherein the adhesive layer further comprises an antimicrobial agent.

19. The mammalian skin covering according to claim 17, wherein the backing layer comprises a film, substrate, or elastic, porous or breathable woven or nonwoven material.

20. The mammalian skin covering according to claim 19, wherein the covering comprises a medical tape, a wound dressing, a bandage of general medicinal utility, or a medical device contacting mammalian skin.

21. A pharmaceutical delivery device comprising: an adhesive layer for contacting mammalian skin and a backing layer, the adhesive layer adhered to the backing layer and comprising a pressure sensitive adhesive composition according to claim 1, and wherein the adhesive layer further comprises a topical, transdermal, or iontophoretic therapeutic agent or pharmaceutical.

22. The pharmaceutical delivery device according to claim 21, wherein the adhesive layer further comprises an excipient, a solvent, or a penetration enhancing agent.

* * * * *